United States Patent [19]

Pinchuk

[11] Patent Number: 4,882,148
[45] Date of Patent: Nov. 21, 1989

[54] CRACK PREVENTION AND IMPROVED THROMBOGENICITY OF IMPLANTED PROSTHESES BY SULFONATION

[75] Inventor: Leonard Pinchuk, Miami, Fla.
[73] Assignee: Corvita Corporation, Miami, Fla.
[21] Appl. No.: 63,537
[22] Filed: Jun. 18, 1987
[51] Int. Cl.$^4$ ............................................. A61K 2/00
[52] U.S. Cl. .................................... 424/423; 424/422; 424/427; 523/112; 604/266; 623/1; 623/4
[58] Field of Search ............... 424/422, 423, 424, 425; 523/112; 604/264, 265, 266, 269

[56] References Cited

U.S. PATENT DOCUMENTS 4,273,873  6/1981  Sugitachi et al. ............... 424/422 X
4,378,435  3/1983  Takagi et al. ........................ 427/2 X
4,475,972  10/1984  Wong ................................... 156/167
4,539,373  9/1985  Mani et al. ....................... 525/913 X

OTHER PUBLICATIONS

Pande, "Thermoplastic Polyurethanes as Insulating Materials for Long-Life Cardiac Pacing Leads", PACE, vol. 6, Sep.-Oct. 1983, Part I, pp. 858-867.
Goldberg et al, "Biocompatibility of Intraocular Lens Polymers", Apr. 1985.
Sulfonation and Related Reactions, Chapter 2, pp. 75-77.
Josefowicz et al, "Heparin-Like Biomaterials", Second World Congress on Biomaterials, 1984.

Primary Examiner—Thurman K. Page
Attorney, Agent, or Firm—Lockwood, Alex, Fitzgibbon & Cummings

[57] ABSTRACT

Implantable devices for medical use are provided which have been subjected to treatment with a crack preventative/antithrombogenic agent in the form of a sulfate. This treatment substantially prevents surface cracking or fissuring of the subcutaneous implantation as well as preventing thrombus formation along the blood contacting surfaces of the treated material.

30 Claims, 1 Drawing Sheet

CRACK PREVENTION AND IMPROVED THROMBOGENICITY OF IMPLANTED PROSTHESES BY SULFONATION

BACKGROUND AND DESCRIPTION OF THE INVENTION

The present invention generally relates to implantable prostheses and to methods for making and treating same to substantially prevent cracking or surface fissuring as well as to provide a nonthrombogenic surface for blood contacting surfaces. More specifically, prostheses made from aromatic polymers such as polyurethane and the like, are treated by sulfonating the aromatic rings of the polymer, the polymeric surface being one that will crack when subjected to subcutaneous implantation for substantial time periods if it is not sulfonated. Additionally, synthetic vascular grafts made from aromatic polymers will experience occlusion of the graft lumen by blood clots, or thrombus, if the polymer is not sulfonated. The sulfonation of such aromatic polymers involves a surface modification of the polymer which is accomplished by the addition of at least one sulfate group ($-SO_3H$) to the aromatic rings of the polymer.

Several biocompatible materials which are quite suitable for use in making implantable medical devices which may be broadly characterized as implantable prostheses exhibit properties which are sought after in such devices. Such properties may include biocompatibility, extrudability, moldability, good fiber forming properties, tensile strength, elasticity, durability, and the like. However, some of these otherwise desirable materials exhibit serious deficiencies when implanted subcutaneously. Such deficiencies include the development of cracks or fissures which, for prostheses comprised of relatively thin strands or members, cause a reduction in the overall strength of the prostheses because of the complete severance of a number of the thin strands or members. Often, surface fissuring or cracking occurs after substantial exposure to body fluids such as are encountered during in vivo implantation and use. Substantial periods of use may be on the order of one month or more or less. Many implantable prostheses are intended to be permanent in nature and should not develop any substantial cracking during years of implantation.

In addition to fissuring or cracking, it is well known that a significant mode of failure of small caliber (less than 7 millimeters in diameter) synthetic vascular grafts is due to the total occlusion of the graft lumen, or blood contacting surface, by blood clots, or thrombus formation. Since many implanted prostheses are intended to be permanent, it is desirable to provide a nonthrombogenic surface for blood contacting prostheses.

Several theories have been promulgated in attempting to define the cause of cracking as well as thrombus formation. Proposed mechanisms to explain the cracking phenomenon include oxidative degradation, hydrolytic instability, enzymatic destruction, mechanical failure, immunochemical mechanisms, and inhibition of lipids. Thrombus formation is believed to occur because of the relative ease with which the anionic platelets adhere to the electrically neutral hydrophobic surface of the graft lumen. The hydrophobic nature of the graft lumen prevents rapid hydration of the lumen thereby maximizing the material blood interface and foreign body reaction.

Prior attempts to control surface fissuring or cracking upon implantation include incorporating antioxidants within the biocompatible polymer and subsequently annealing the biocompatible polymer under various conditions, typically including attempting to remove stresses within the polymer by applications of various heating and cooling conditions. Attempts such as these have been largely unsuccessful. It is known in the art that the treatment of certain polymers with certain sulfur containing materials greatly increases or enhances the nonthrombogenicity of the polymer material. In particular, it is known that sulfonated polystyrene demonstrates antithrombogenic activity which is directly related to the surface density of sulfonate groups. However, these known effects are generally accomplished by sulfonation in a manner other than that which is disclosed herein.

Regarding both cracking and nonthrombogenicity, a particular need is evident when attempting to form prostheses with procedures including the extrusion or spinning of polymer fibers, as are involved in winding fiber-forming polymers into porous vascular grafts, such as described in U.S. Pat. No. 4,475,972, the subject matter thereof being incorporated by reference herein. Such vascular grafts include a plurality of strands that are of a somewhat fine diameter such that when cracking occurs after implantation, the cracking is manifested in the form of complete severance of various strands of the vascular graft. Such strand severance cannot be tolerated to any substantial degree when the purpose behind implantation is to provide a fairly permanent graft implant whereby the vascular graft remains viable for a number of years. Likewise, thrombogenicity will often manifest itself in small caliber vascular grafts (less than 7 millimeters in diameter) in the form of total occlusion of the graft lumen. As discussed above in terms of strand breakage and cracking, vascular graft occlusion cannot be tolerated if such grafts are to remain viable for indefinite periods of time.

Numerous vascular graft structures made from spun fibers appear to perform very well insofar as their ability to withstand physical stress conditions which approximate those experienced during and after implantation, including stresses imparted by sutures and the like. For example, certain aromatic polyurethane spun grafts when subjected to constant stress under in vitro conditions, such as in saline solution at body temperature, do not demonstrate the cracking that is evident when substantially the same polyurethane spun graft is subjected to in vivo conditions. Accordingly, while many materials, such as polyurethane, polyester terephthalate, polystyrene, polysulfone and the like, may appear to provide superior medical devices or prostheses when subjected to stress under in vitro conditions, these materials are found to be unsatisfactory when subjected to substantially the same types of stresses but under in vivo conditions.

There is accordingly a need for a treatment which will impart crack preventive properties to aromatic polymers that experience surface fissuring under in vivo conditions as well as imparting antithrombogenic properties to the blood contacting surfaces of such polymers which make up synthetic vascular grafts. Both properties, anticracking and antithrombogenicity, must be available to the treated vascular grafts or prostheses so that cracking and thrombus formation can be successfully avoided after implantation for a period of months or years. Exemplary medical devices or prostheses for which such a treatment would be medically advantageous include vascular grafts, introacular lens loops or haptics, pacemaker lead insulators, permanent sutures, diaphragms for artificial hearts, prosthetic heart valves, and the like.

Objectives of the type mentioned above are met by the present invention which achieves a successful treatment of biocompatible aromatic polymers including polyurethane, polyester terephthalate, polystyrene, polysulfone, aromatic silicone rubbers, and the like so that these treated polymers will not exhibit surface cracking or fissuring under in vivo conditions and to the extent that these treated polymers will exhibit antithrombogenic properties when used as blood contacting surfaces. The invention involves treating the aromatic polymers with a sulfonating agent. Such sulfonating agents include sulfur trioxide vapor and concentrated or fuming sulfuric acid. Most preferably, the sulfonating agent is in the form of an adduct of sulfur trioxide and a primary alcohol. Treatment of a prosthesis with the sulfonating agent can be carried out by a procedure as straight forward as dipping the prosthesis into the sulfonating agent or, in the case of sulfur trioxide vapor, by directly exposing the prosthesis to the sulfur trioxide vapor. It should be noted that the use of sulfur trioxide vapor or concentrated or fuming sulfuric acid is not the preferred treatment for sulfonating fine porous networks, such as filamentous spun polyurethane grafts, because such porous networks generally cannot withstand the heats of reaction from these concentrated sulfonating agents which tend to melt or distort the porous network before the sulfonation reaction is complete. For this reason, a more mild reaction is preferred, such as the reaction between a aromatic polymer and an adduct made from a primary alcohol and sulfur trioxide. Following sulfonation, steps are taken to neutralize residual acid and ionize the resultant sulfate moiety such as by immersing the prostheses in a basic solution containing sodium carbonate or the like. Sulfonation of the polymer can be confirmed by staining the prostheses with a sulfate sensitive dye such as methylene blue.

It is accordingly an object of this invention to provide an improved implanted device, method of its production, and treatment to prevent both cracking and thrombus formation.

Another object of the present invention is to provide an improved vascular graft made from spun fibers and exhibiting an exceptional ability to prevent crack formation, strand severance, and occlusion due to thrombus formation after subcutaneous implantation for substantial periods of time such as those experienced in generally permanent implantation procedures.

Another object of the present invention is to provide an improved production method, treatment method and treated product that imparts the properties of in vivo crack prevention and nonthrombogenicity to biocompatible polymeric materials that exhibit desirable medical properties but otherwise experience cracking and thrombogenicity in in vivo applications.

These and other objects, features and advantages will be clearly understood through a consideration of the following detailed description.

BRIEF DESCRIPTION OF THE DRAWINGS

In the course of this description, reference will be made to the attached drawings, wherein.

DESCRIPTION OF THE PARTICULAR EMBODIMENTS

Figure 1:
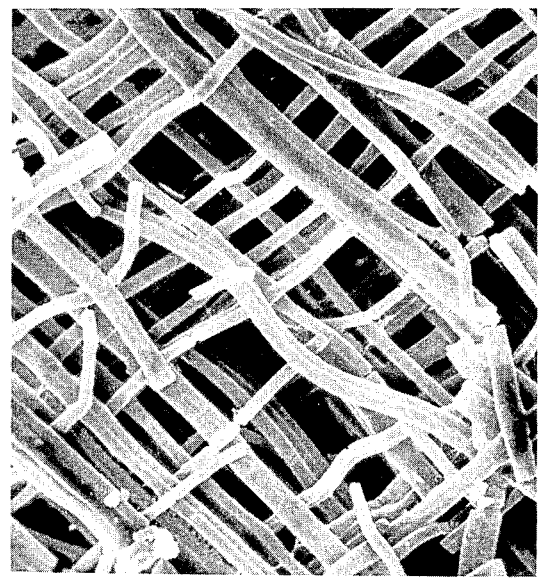
FIG. 1 is a photomicrograph of a section of a vascular graft after a period of in vivo use, the graft having been made by spinning a polyurethane not treated in accordance with this invention.

Crack preventative/antithrombogenic materials in accordance with the present invention are of the sulfur trioxide type and are most easily provided in the form of concentrated or fuming sulfuric acid, or in the form of a solution containing sulfur trioxide dissolved in a primary alcohol such as methanol, ethanol, or ethanol which has been denatured with methanol. When the prosthesis requiring sulfonation is made of a fine porous network, as in FIGS. 1 and 2, it is necessary to consider the possibility of melting or distorting of the polymer fibers when exposed to concentrated or fuming sulfuric acid. In such cases, melting or distortion of the fibers can be avoided by sulfonating such a fine porous network with a crack preventative/antithrombogenic material consisting of sulfur trioxide dissolved in a primary alcohol.

With more particular reference to the crack preventative/antithrombogenic material, the sulfur component is preferably in the form of a sulfur trioxide which can be represented by the formula $SO_3$. When either concentrated or fuming sulfuric acid, or sulfur trioxide vapors are used as the crack preventative/antithrombogenic agent, the sulfur trioxide is presumed to react directly with the aromatic polymer which is further treated with a mild base, such as 2% sodium carbonate, to give the sodium salt. An exemplary sulfonated polymer is the sodium salt of sulfonated aromatic polyurethane which can be represented by the following formula:

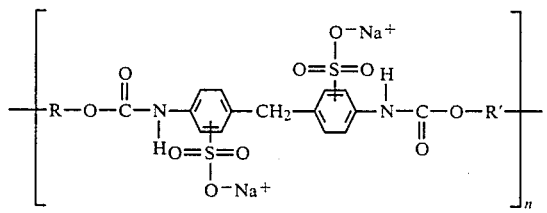

where R and R' are generally alkyl groups and R may be the same as R'; and n is an integer greater than 1.

Similarly, sulfonation of the aromatic rings can be accomplished in the same manner for other polymers such as polyester terephthalate, polystyrene, polysulfone, and aromatic silicone rubber. The basic sulfonation reactions and method of treatment are substantially the same for all these polymers. In each case, the sulfonated polymer is believed to contain one sulfur trioxide moiety per aromatic group. Preferably, the sulfonation step is followed by treatment of the sulfonated prostheses with a mild base, such as a 2% solution of sodium carbonate, to neutralize residual acid and to ionize the resultant sulfur trioxide moiety. In this manner, the surface of the prosthesis is rendered extremely hydrophilic and anionic.

When it is desirable to sulfonate fine porous networks, such as filamentous spun aromatic polyurethane grafts, it is typically necessary to use an adduct made from a primary alcohol and sulfur trioxide for such sulfonation in order to avoid melting or distortion of the spun polymer as often will occur when fuming or concentrated acid is used. The adduct utilized is selected so as to render the aromatic polymer hydrophilic without damaging it by dissolution or severe swelling. The adduct is preferably comprised of the Lewis complex of sulfur trioxide and a primary alcohol such as methanol, ethanol, 1-propanol, 1-butanol, or the like.

It is generally known that the sulfur atom on the sulfur trioxide moiety is an electrophile, or a Lewis acid, and will combine with a nucleaophile, or Lewis base, to form coordination compounds or adducts. In the case of an adduct of sulfur trioxide and ethanol, it is believed that the reaction can be depicted as follows:

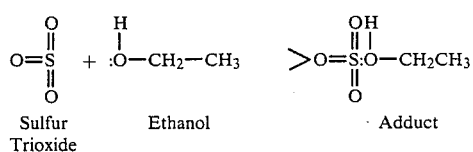

Sulfur Trioxide    Ethanol    Adduct

Upon sulfonation of an organic compound, the sulfur trioxide is believed to be released from the alcohol so that it may react with the aromatic group of the polymer to form the salt of the new acid. Further treatment with a mild base, such as sodium carbonate, yields the sodium salt of the sulfonated polymer. In the case of aromatic polyurethane, the reaction can be depicted as follows:

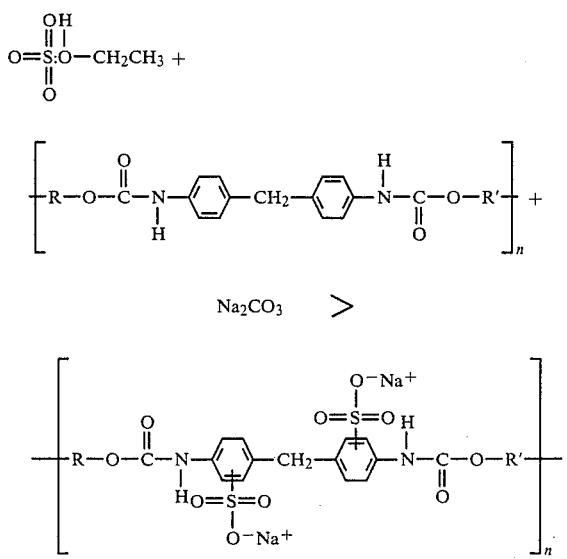

Other adducts for sulfonating aromatics in solution are known, such as sulfur trioxide in tetrahydrofuran, ethylene triamine, triethyl phosphate, dimethyl formamide, and dimethyl acetamide. However, in the case of polyurethane, these other adducts generally should not be used alone because they also act as good solvents for finely porous polyurethane and tend to dissolve the prosthesis before the reaction is complete.

The sulfonation of aromatic polymers with fuming sulfuric acid may be accomplished without significant concern for melting of the polymer when the implantable device has a relatively large and smooth surface area, such as would be the case for a cardiac lead insulator or an artificial heart diaphragm which present a unitary surface area that is generally smooth and without any significant undulations or porosity. In these instances, sulfonation may be accomplished by submerging the aromatic polymer in a beaker of fuming sulfuric acid which has been previously cooled to 0°–10° C. in an ice bath or the like. The polymer should remain submerged in the acid for about 5 to 10 seconds, depending on the material used to make the prosthesis. In the case of aromatic polyurethanes, for example, sulfonation is very rapid and is evidenced by a dramatic color change to a bright orange-red. The polymer may then be removed from the acid and, if desired, be quenched by immersion in distilled water for 30 seconds, more or less. The polymer is then soaked in a weak base, such as a 2% solution of sodium carbonate, for approximately 1 minute. Extractables may then be leached out by soaking the sulfonated polymer in distilled water for a few hours. The presence of sulfate groups can be confirmed by soaking the polymer in a sulfide sensitive dye. Suitable dyes include methylene blue or toluidine blue in 0.1%–0.2% solutions. By soaking the sulfonated polymer in the dye solution for 2 minutes, followed by rinsing the prosthesis with distilled water, the sulfonated prosthesis should be stained blue. Non-sulfonated polymers will not stain.

Additionally, in lieu of using fuming sulfuric acid, sulfonation may be accomplished by exposing the selected prosthesis directly to sulfur trioxide vapor or by using concentrated sulfuric acid. Where concentrated sulfuric acid is used, water contamination must be kept below the 20% level in order to avoid dissolution of the prosthesis, especially in the case of aromatic polyurethanes. When sulfur trioxide vapors or concentrated sulfuric acid are used to sulfonate the prosthesis, it may be necessary to slightly increase the time in which the polymers are exposed to either the concentrated acid or the sulfate vapor so that an effective exposure time may exceed the time required when fuming sulfuric acid is utilized. In the case of sulfur trioxide vapors, the requirement of the sulfuric acid treatment to cool the temperature to about 0°–10° C. does not apply. Following sulfonation with either sulfate vapor or concentrated acid, subsequent steps in the preparation of the prosthesis are identical to those described above with respect to using fuming sulfuric acid for sulfonated purposes. In this manner, the resulting sulfonated prosthesis will be rendered crack resistant to in vivo crack development while simultaneously possessing antithrombogenic properties.

Where the prosthesis incorporates a fine porous network, such as a filamentous spun polyurethane vascular graft, a sulfonation reaction which is milder than that suitable for less delicate structures is desired to avoid melting of the prosthesis during sulfonation. Such milder sulfonation conditions are preferably achieved by the use of an adduct of sulfur trioxide and a primary alcohol. With specific reference to the use of ethanol as the primary alcohol employed, the adduct typically is prepared by charging a flask, such as an Erlenmeyer flask, with 80 milliliters (80 ml) of pure ethanol. Alternatively, ethanol denatured with methanol may be used. However, ethanol denatured with isopropanol or other secondary alcohols, should not be used since such secondary alcohols may be degraded by the sulfonic acid.

The alcohol containing flask should be cooled, such as by placing the flask in an ice bath or the like. Fuming sulfuric acid is added dropwise while the alcohol is constantly stirred by a magnetic stir bar or its equivalent. The rate at which the fuming sulfuric acid is added to the ethanol should be such that the exotherm caused by the alcohol/acid reaction remains below 70° C. Therefore, close monitoring of the temperature of the adduct solution is required.

Typically, a maximum of 20 milliliters (20ml) of acid can be added to the 80 milliliters of alcohol. In this manner, an adduct of sulfur trioxide and alcohol is produced and is dissolved in excess alcohol. Where larger quantities of adduct are required, the actual amounts of alcohol and fuming sulfuric acid may be increased in relative proportion to the amount disclosed above. Also, these amounts are typically those that are most advantageously employed when the alcohol is ethanol. When alcohols other than ethanol are employed to make the adduct, the relative proportions of fuming sulfuric acid and alcohol may be varied somewhat as needed. When methanol is used, for example, a 30% (by volume) solution of acid in methanol is desired. Further, the sulfuric acid/methanol exotherm is quite violent, requiring that the sulfuric acid be added very slowly to the methanol bath.

Sulfonation of a prosthesis using a sulfur trioxide/alcohol adduct typically is achieved by heating the adduct solution to a temperature in the range of about 70°–80° C. and immersing the prosthesis in the heated adduct solution for at least approximately 2 minutes. Following exposure to the adduct, the prosthesis may be rinsed with distilled water, if desired, and then submerged or rinsed in a mild base solution, such as 2% sodium carbonate. Rinsing or submersion in base typically is necessary to neutralize excess acid from the adduct solution. Following exposure to the mild base, the prosthesis should again be rinsed with distilled water. As in the case of sulfonation with fuming sulfuric acid, the presence of sulfonate in the adduct-treated prosthesis may be confirmed by staining with methylene blue or toluidine blue.

According to the invention, prostheses composed of sulfonated aromatic polymers possess surfaces which are both hydrophilic and anionic. Prior to sulfonation, the surfaces are generally hydrophobic and electrically neutral. In this manner, the sulfonated blood contacting surfaces possess a resistance to in vivo thrombus formation which nonsulfonated surfaces of the same aromatic polymers do not possess. Although the exact mechanism for prevention of thrombus formation is not known, it has been theorized that the anionic nature of the sulfonated surface tends to limit platelet deposition and thrombus formation due to the repulsion of anionic platelets. Additionally, the hydrophilic nature of the sulfonated surface provides for rapid hydration thereby coating the surface with water and reducing the material blood interface and foreign body reaction.

Similarly, prostheses composed of sulfonated aromatic polymers prepared according to this invention exhibit in vivo resistance to cracking or fissuring. The exact nature of the mechanism for crack prevention is not presently known. However, it has been theorized that the bulky sulfur trioxide moieties protect the polymer linkages from enzymatic degradation by the mechanism of steric hindrance.

The following examples are illustrative of the crack prevention and antithrombogenicity that are exhibited by sulfonated aromatic prostheses according to this invention.

EXAMPLE 1

A polyurethane dissolved in dimethyl acetamide was spun onto a rotating mandrel to form a cylindrical synthetic graft generally as described in U.S. Pat. No. 4,475,972. The diameter of the fibers comprising the graft was approximately 8 microns. The graft was annealed for 48 hours under alternations of nitrogen and vacuum at 80° C. and then cut into eight pieces. Two pieces served as untreated controls, the rest were subjected to three different surface modifications (two samples each), one of them being the sulfonation reaction using the sulfur trioxide/ethanol adduct as described above. These graft segments were then ethylene oxide sterilized and implanted subcutaneously in a dog. After one month the samples were explanted, cleaned in sodium hydroxide and sodium hypochlorite solution and then examined under a scanning electron microscope for fiber breakage and cracking. Sections of the graft were also manually pulled apart and their relative tensile strengths noted. Non-implanted, similarly modified grafts were also examined for comparison purposes.

Figure 2:
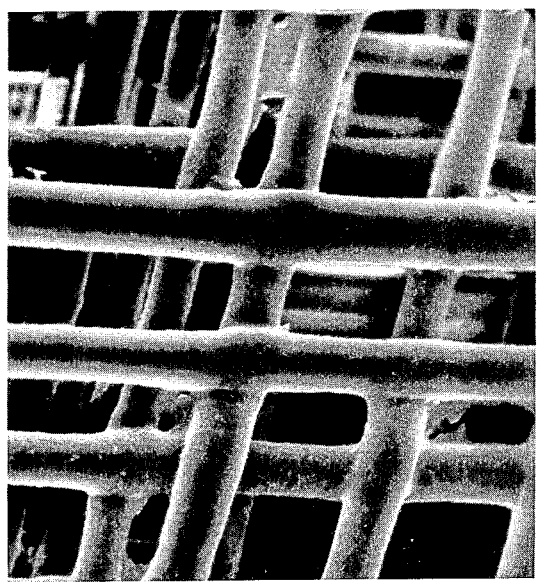
FIG. 2 is a photomicrograph of another section from a spun polyurethane graft used in FIG. 1 and after in vivo use but which had been treated in accordance with this invention prior to subcutaneous implantation.

All of the above graft segments except for those containing the sulfonation modification exhibited severe cracking, fiber breakage and almost total loss of tensile strength. FIG. 1 is a reproduction of a photomicrograph of one of the explanted grafts which was not treated with the sulfur trioxide/ethanol adduct prior to implanation. FIG. 1 illustrates the cracking problem exhibited in the unsulfonated grafts. The sulfonated samples did not demonstrate any cracking and exhibited a tensile strength similar to that of a non-implanted control. FIG. 2 is a reproduction of a photomicrograph of one of the grafts which had been treated with the sulfur trioxide/ethanol adduct prior to implanation, the treated and explanted graft exhibiting no noticeable cracking or fiber breakage.

EXAMPLE 2

Several vascular grafts having a diameter of 6 millimeters and a length of 5 centimeters were made as described in Example 1. The grafts were treated with silicone rubber or surface modified by the sulfonation reaction utilizing the sulfur trioxide/ethanol adduct previously described. These grafts, as well as control grafts without surface modification, were implanted as aorto-iliac bypass grafts in dogs for one month. The silicone grafts did not remain patent but occluded within a few days after implantation. They did remain intact with no breakage of fibers for the one month duration of the experiment. The untreated control grafts remained essentially occlusion free for the first few weeks and then disintegrated due to fiber breakage by the end of the month. The sulfonated grafts remained both occlusion free and crack free throughout the experiment.

It will be understood that the embodiments of the present invention which have been described are illustrative of some of the applications of the principles of the present invention. Numerous modifications may be made by those skilled in the art without departing from the true spirit and scope of the invention as defined in the following claims.

I claim:

1. A treatment method for substantially preventing in vivo cracking of biocompatible surfaces of implanted devices for medical use, consisting essentially of:
   providing a shaped substrate of an implantable medical device having a biocompatible polymeric surface that is susceptible to cracking when subjected to subcutaneous implantation under in vivo conditions for substantial time periods, such in vivo conditions including those that promote crack-forming biodegradation of said biocompatible polymeric surface;
   applying a crack preventive composition to said biocompatible polymeric surface, said crack preventive composition including a sulfonating agent, said sulfonating agent is selected from the group consisting of fuming sulfuric acid, concentrated sulfuric acid, sulfur trioxide vapors, and blends thereof with an alcohol or a blend of alcohols;
   reacting said sulfonating agent with said biocompatible polymeric surface in order to substantially prevent in vivo cracking of said surface without requiring any additional treatment of said surface; and
   said providing step includes selecting said substrate to contain a polymeric structure which contains aromatic moieties.

2. The treatment method of claim 1 wherein said biocompatible polymeric surface is selected from the group consisting of aromatic polyurethanes, polyester terephthalates, polystyrenes, polysulfones and aromatic silicon rubbers.

3. The treatment method of claim 1 wherein said biocompatible polymeric surface is constructed of a unitary surface area of said biocompatible polymer.

4. The treatment method according to claim 1 wherein the crack preventive composition will not dissolve substantial portions of said biocompatible polymeric surface.

5. The treatment method according to claim 1 wherein the crack preventive composition is the product obtained by the addition of fuming sulfuric acid to one or more primary alcohols.

6. The treatment method of claim 1 wherein the crack preventive composition is made by the addition of sulfuric acid to ethanol.

7. The treatment method of claim 1 wherein the crack preventive composition is made by the addition of sulfuric acid to ethanol, said ethanol being blended with methanol.

8. The treatment method of claim 1 wherein the crack preventive composition is made by the addition of sulfuric acid to methanol.

9. The treatment method of claim 1 wherein said biocompatible polymeric surface is constructed of one or more strands of said biocompatible polymer.

10. The treatment method of claim 1 wherein said biocompatible polymeric surface is an aromatic polyurethane.

11. The treatment method of claim 1, wherein said in vivo conditions promote thrombus formation, and the device thus treated remains patent under such in vivo conditions.

12. A treatment method for substantially preventing in vivo thrombosis of biocompatible surfaces of synthetic vascular grafts, consisting essentially of:
    providing a shaped substrate of an implantable medical device having a biocompatible polymeric surface that is susceptible to thrombus formation when contacted with blood under in vivo conditions for substantial time periods, said in vivo conditions including those that promote thrombosis of said biocompatible polymeric surface;
    applying an antitrombogenic composition to said biocompatible polymeric surface, said antitrombogenic composition being made by the addition of a sulfur trioxide source to a primary alcohol;
    reacting said antitrombogenic composition with said biocompatible polymeric surface in order to substantially prevent in vivo thrombosis on said surface without requiring any additional treatment of said surface; and
    said providing step includes selecting said substrate to contain a polymeric structure which contains aromatic moieties.

13. The treatment method of claim 12, wherein said biocompatible surface is an aromatic polymer selected from the group consisting of aromatic polyurethanes, polyester terephthalates, polystyrenes, polysulfones and aromatic silicone rubbers.

14. The treatment method of claim 12, wherein said biocompatible surface is an aromatic polyurethane.

15. The treatment method of claim 12, wherein the biocompatible surface includes one or more extruded fibers that are shaped by winding over a mandrel.

16. The treatment method of claim 12, wherein the primary alcohol in said antithrombogenic composition is ethanol.

17. The treatment method of claim 12 wherein the primary alcohol in said antithrombogenic composition is ethanol denatured with methanol.

18. The treatment method of claim 12 wherein the primary alcohol in said antithrombogenic composition is methanol.

19. The treatment method of claim 12, wherein said in vivo conditions include exposure of at least part of said biocompatible polymeric surface to blood to form blood clots or thrombus.

20. The treatment method of claim 12, wherein the antithrombogenic composition will not dissolve substantial portions of said biocompatible polymeric surface.

21. The treatment method of claim 12, wherein the sulfur trioxide source is sulfuric acid.

22. An implantable device for medical use under in vivo conditions, consisting essentially of:
    a shaped substrate of an implantable medical device having a biocompatible polymeric surface that is susceptible to biodegradation cracking when subjected to subcutaneous implantation under in vivo conditions for substantial periods of time;
    said biocompatible polymeric surface further being susceptible to clotting or thrombus formation when contacted with blood under in vivo conditions for substantial periods of time;
    a crack preventative/antithrombogenic agent applied to said substrate, said crack preventative/antithrombogenic agent including sulfur trioxide; and
    said biocompatible polymeric surface is resistant to cracking and to thrombus formation under in vivo conditions after said crack preventative/antitrombogenic agent is applied thereto and reacted therewith in order to substantially prevent in vivo cracking and in vivo thrombosis of said surface without requiring any additional treatment of said biocompatible polymeric surface.

23. The implantable device according to claim 22, wherein said biocompatible polymeric surface is selected from of group consisting the aromatic polyurethanes, polyester terephthalates, polystyrenes, polysulfones, and aromatic silicone rubbers.

24. The implantable device according to claim 22, wherein said biocompatible polymeric surface is an aromatic polyurethane.

25. The implantable device according to claim 22, wherein said biocompatible polymeric surface includes one or more extruded fibers that are shaped by winding over a mandrel.

26. The implantable device according to claim 22, wherein said biocompatible polymeric surface includes one or more strands of said biocompatible polymer.

27. The implantable device according to claim 22, wherein said biocompatible polymeric surface is in the shape of a vascular graft.

28. The implantable device according to claim 22, wherein said crack preventative/antithrombogenic agent, prior to its application to said biocompatible polymeric surface, includes sulfuric acid.

29. The implantable device according to claim 22, wherein said crack preventative/antithrombogenic agent, prior to its application to said biocompatible polymeric surface, is made by the addition of sulfuric acid to a primary alcohol.

30. The implantable device according to claim 22, wherein said biocompatible polymeric surface is in the shape of a cardiac lead insulator.

* * * * *

UNITED STATES PATENT AND TRADEMARK OFFICE
CERTIFICATE OF CORRECTION

PATENT NO. : 4,882,148

DATED : November 21, 1989

INVENTOR(S) : Leonard Pinchuk

It is certified that error appears in the above-identified patent and that said Letters Patent is hereby corrected as shown below:

Col. 9, line 8, "such" should read --said--.

Col. 10, lines 64-65, "antitrombogenic" should read --antithrombogenic--.

Col. 11, line 3, "of group consisting the" should read --the group consisting of--.

Signed and Sealed this

Thirteenth Day of August, 1991

Attest:

HARRY F. MANBECK, JR.

Attesting Officer  Commissioner of Patents and Trademarks